(12) United States Patent
Shiber

(10) Patent No.: US 6,818,002 B2
(45) Date of Patent: Nov. 16, 2004

(54) VESSEL CLEANER AND BARRIER

(76) Inventor: Samuel Shiber, 365 Kearney Cir., Manchester, NH (US) 03104

( * ) Notice: Subject to any disclaimer, the term of this patent is extended or adjusted under 35 U.S.C. 154(b) by 262 days.

(21) Appl. No.: 10/252,290

(22) Filed: Sep. 23, 2002

(65) Prior Publication Data

US 2003/0028206 A1 Feb. 6, 2003

Related U.S. Application Data

(63) Continuation-in-part of application No. 10/086,465, filed on Mar. 1, 2002, now Pat. No. 6,767,353, which is a continuation-in-part of application No. 09/867,307, filed on May 29, 2001, now Pat. No. 6,758,851, which is a continuation-in-part of application No. 09/654,934, filed on Sep. 1, 2000, now Pat. No. 6,482,215, which is a continuation-in-part of application No. 09/389,712, filed on Sep. 3, 1999, now Pat. No. 6,143,009, which is a continuation-in-part of application No. 09/241,802, filed on Feb. 2, 1999, now abandoned.

(51) Int. Cl.[7] .............................................. A61B 17/32
(52) U.S. Cl. ....................................................... 606/159
(58) Field of Search ................................ 606/159, 170, 606/174, 167, 180; 604/22

(56) References Cited

U.S. PATENT DOCUMENTS

| 4,228,802 A | 10/1980 | Trott |
| 4,772,258 A | 9/1988 | Marangoni |
| 4,857,046 A | 8/1989 | Stevens et al. |
| 4,986,807 A | 1/1991 | Farr |
| 4,994,067 A | 2/1991 | Summers |
| 5,002,553 A | 3/1991 | Shiber |
| 5,007,896 A | 4/1991 | Shiber |
| 5,009,659 A | 4/1991 | Hamlin et al. |
| 5,011,490 A | 4/1991 | Fischell et al. |
| 5,024,651 A | 6/1991 | Shiber |
| 5,026,384 A | 6/1991 | Farr et al. |
| 5,059,203 A | 10/1991 | Husted |
| 5,074,841 A | 12/1991 | Ademovic et al. |
| 5,087,265 A | 2/1992 | Summers |
| 5,097,849 A | 3/1992 | Kensey et al. |
| 5,100,426 A | 3/1992 | Nixon |
| 5,102,415 A | 4/1992 | Guenther |
| 5,116,350 A | 5/1992 | Stevens |
| 5,135,531 A | 8/1992 | Shiber |
| 5,154,724 A | 10/1992 | Andrews |
| 5,158,564 A | 10/1992 | Schnepp-Pasch et al. |
| 5,192,268 A | 3/1993 | Shiber |
| 5,192,291 A | 3/1993 | Pannek |
| 5,201,750 A | 4/1993 | Hocherl et al. |
| 5,205,822 A | 4/1993 | Johnson |
| 5,217,474 A | 6/1993 | Zacca et al. |
| 5,232,445 A | 8/1993 | Bonzel |
| 5,234,451 A | 8/1993 | Ospyka |

(List continued on next page.)

Primary Examiner—Kevin T. Truong
(74) Attorney, Agent, or Firm—Samuel Shiber

(57) ABSTRACT

A rotary flexible agitator system for removing an obstruction from within a patient's vessel that a motor-driven rotary flexible agitator-shaft disposed in the tubular housing, the agitator-shaft having an offset distal-agitator attached to its distal end that extends out of the open distal end, the effective diameter of the offset distal-agitator being substantially larger than its cross-sectional diameter, wherein rotating the offset distal-agitator breaks the obstruction in the vessel to pieces and the relative motion between the rotary flexible agitator-shaft and the flexible tube reduces the longitudinal friction that may resist the movement of the pieces through the flexible tube; and a catheter in which the flexible tube is disposed and guided into the vessel having a barrier at its distal end section for temporarily blocking flow through the vessel and reducing the likelihood of distal embolization.

3 Claims, 3 Drawing Sheets

U.S. PATENT DOCUMENTS

| | | |
|---|---|---|
| 5,242,460 A | 9/1993 | Klein et al. |
| 5,242,461 A | 9/1993 | Kortenbach et al. |
| 5,248,296 A | 9/1993 | Alliger |
| 5,250,059 A | 10/1993 | Andreas et al. |
| 5,261,877 A | 11/1993 | Fine et al. |
| 5,269,751 A | 12/1993 | Kaliman et al. |
| 5,282,484 A | 2/1994 | Reger |
| 5,284,486 A | 2/1994 | Kotula et al. |
| 5,290,232 A | 3/1994 | Johnson |
| 5,306,244 A | 4/1994 | Shiber |
| 5,312,425 A | 5/1994 | Evans et al. |
| 5,312,427 A | 5/1994 | Shturman |
| 5,314,438 A | 5/1994 | Shturman |
| 5,334,211 A | 8/1994 | Shiber |
| 5,336,167 A | 8/1994 | Sullivan et al. |
| 5,350,390 A | 9/1994 | Sher |
| 5,356,418 A | 10/1994 | Shturman |
| 5,358,472 A | 10/1994 | Vance et al. |
| 5,358,485 A | 10/1994 | Vance et al. |
| 5,358,509 A | 10/1994 | Fine et al. |
| 5,366,464 A | 11/1994 | Belknap |
| 5,368,603 A | 11/1994 | Halliburton |
| 5,370,609 A | 12/1994 | Drasler et al. |
| 5,370,651 A | 12/1994 | Summers |
| 5,370,653 A | 12/1994 | Cragg |
| 5,376,100 A | 12/1994 | Lefebvre |
| 5,395,311 A | 3/1995 | Andrews |
| 5,402,790 A | 4/1995 | Jang et al. |
| 5,403,334 A | 4/1995 | Evans et al. |
| 5,417,703 A | 5/1995 | Brown et al. |
| 5,419,774 A | 5/1995 | Willard et al. |
| 5,423,799 A | 6/1995 | Shiu |
| 5,441,510 A | 8/1995 | Simpson et al. |
| 5,449,369 A | 9/1995 | Imran |
| 5,490,859 A | 2/1996 | Mische et al. |
| 5,501,694 A | 3/1996 | Ressemann et al. |
| 5,507,292 A | 4/1996 | Jang et al. |
| 5,507,760 A | 4/1996 | Wynne et al. |
| 5,507,761 A | 4/1996 | Duer |
| 5,512,044 A | 4/1996 | Duer |
| 5,514,151 A | 5/1996 | Fogarty et al. |
| 5,522,824 A | 6/1996 | Ashby |
| 5,522,825 A | 6/1996 | Kropf et al. |
| 5,522,826 A | 6/1996 | Daily |
| 5,527,326 A | 6/1996 | Hermann et al. |
| 5,540,707 A | 7/1996 | Ressemann et al. |
| 5,554,114 A | 9/1996 | Wallace |
| 5,554,163 A | 9/1996 | Shturman |
| 5,556,405 A | 9/1996 | Lary |
| 5,556,408 A | 9/1996 | Farhat |
| 5,569,275 A | 10/1996 | Kotula et al. |
| 5,569,277 A | 10/1996 | Evans et al. |
| 5,571,130 A | 11/1996 | Simpson et al. |
| 5,584,843 A | 12/1996 | Wulfman et al. |
| 5,626,593 A | 5/1997 | Imran |
| 5,630,823 A | 5/1997 | Schmitz-Rode et al. |
| 5,632,755 A | 5/1997 | Nordgren et al. |
| 5,643,296 A | 7/1997 | Hundertmark et al. |
| 5,643,297 A | 7/1997 | Nordgren et al. |
| 5,643,298 A | 7/1997 | Nordgren et al. |
| 5,649,941 A | 7/1997 | Lary |
| 5,653,722 A | 8/1997 | Kieturakis |
| 5,658,301 A | 8/1997 | Lemaitre et al. |
| 5,658,302 A | 8/1997 | Wicherski et al. |
| 5,662,603 A | 9/1997 | Gelbfish |
| 5,669,920 A | 9/1997 | Conley |
| 5,674,232 A | 10/1997 | Halliburton |
| 5,681,336 A | 10/1997 | Clement et al. |
| 5,688,234 A | 11/1997 | Frisbie |
| 5,690,642 A | 11/1997 | Osborne |
| 5,695,506 A | 12/1997 | Pike et al. |
| 5,695,507 A | 12/1997 | Auth |
| 5,695,508 A | 12/1997 | Chigogidze |
| 5,702,413 A | 12/1997 | Lafontaine |
| 5,755,775 A | 5/1998 | Trerotola |
| 5,766,191 A | 6/1998 | Trerotola |
| 5,772,674 A | 6/1998 | Nakhjavan |
| 5,779,721 A | 7/1998 | Nash |
| 5,785,675 A | 7/1998 | Drasler |
| 5,792,157 A | 8/1998 | Mische |
| 5,827,229 A | 10/1998 | Auth |
| 5,836,868 A | 11/1998 | Ressemann |
| 5,843,022 A | 12/1998 | Willard |
| 5,843,103 A | 12/1998 | Wulfman |
| 5,873,882 A | 2/1999 | Straub |
| 5,876,414 A | 3/1999 | Straub |
| 5,879,361 A | 3/1999 | Nash |
| 5,897,534 A | 4/1999 | Heim |
| 6,090,118 A | 7/2000 | McGuckin |
| 6,206,898 B1 | 3/2001 | Honeycutt et al. |
| 6,235,042 B1 | 5/2001 | Katzman |
| 6,758,851 B2 * | 7/2004 | Shiber ........................ 606/159 |
| 6,767,353 B1 * | 7/2004 | Shiber ........................ 606/159 |

* cited by examiner

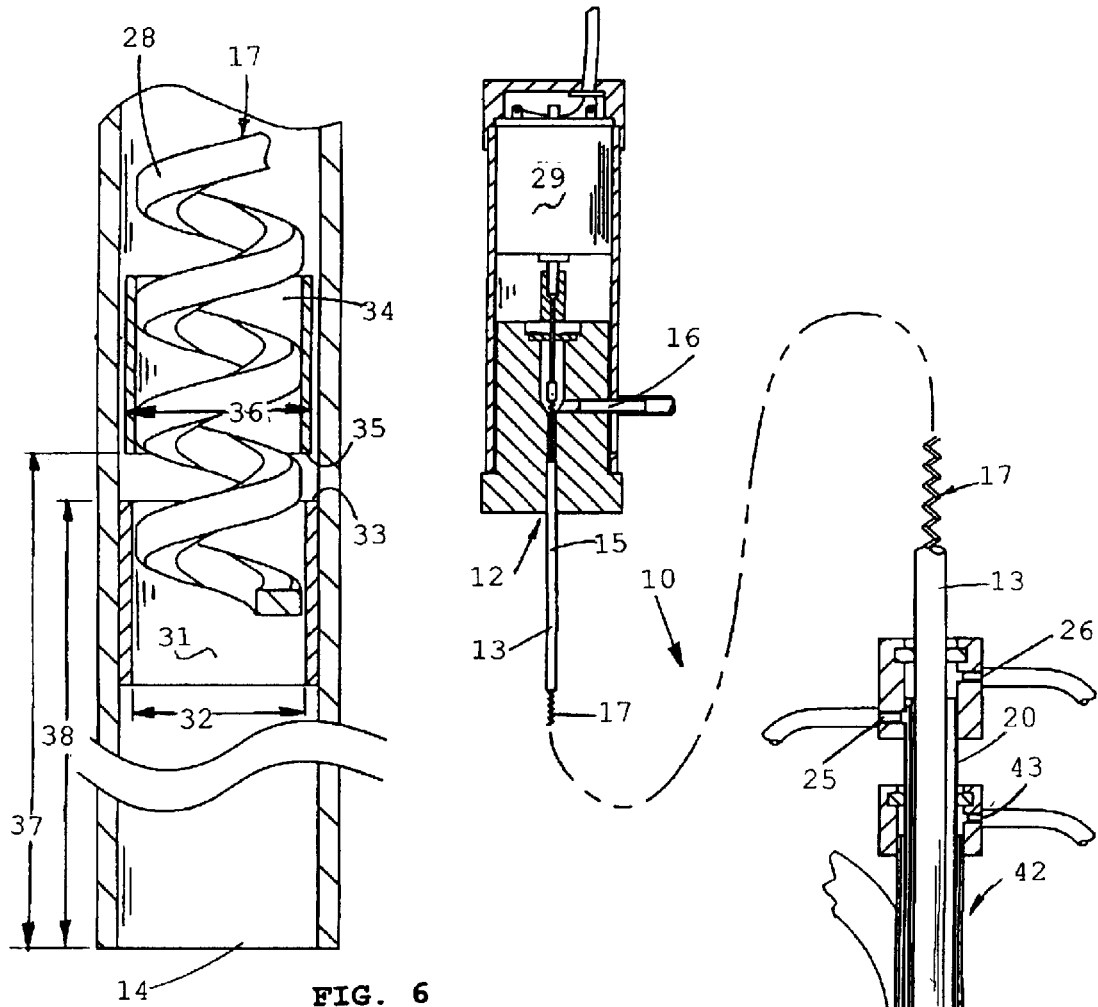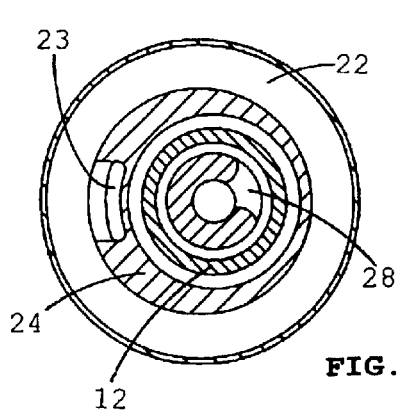

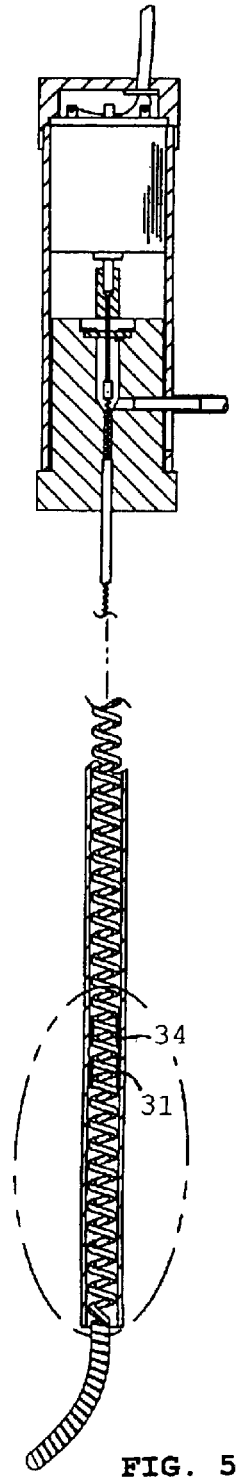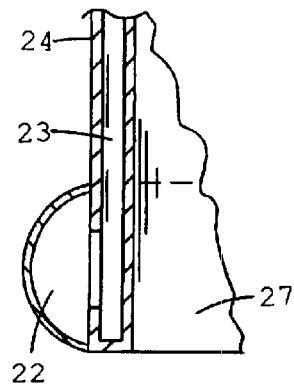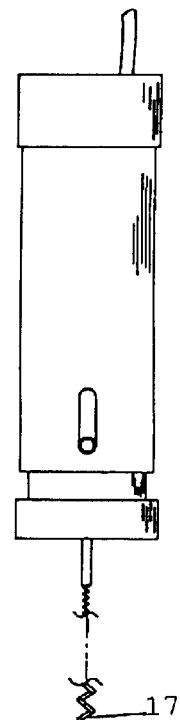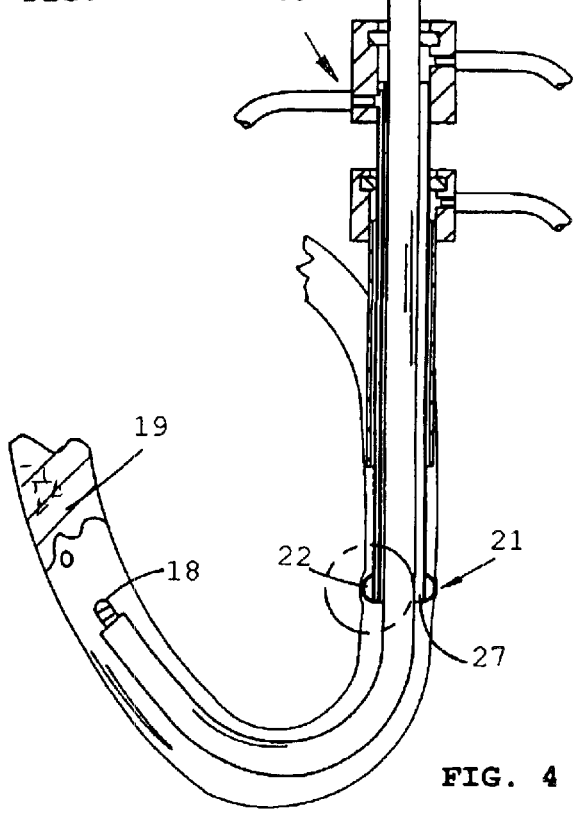
FIG. 3
FIG. 5
FIG. 4

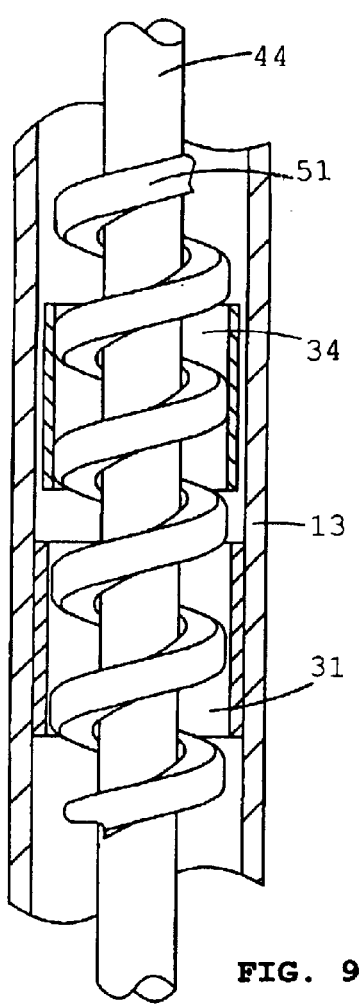
FIG. 9
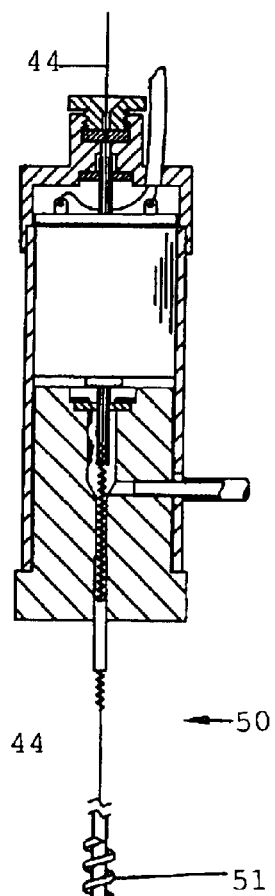
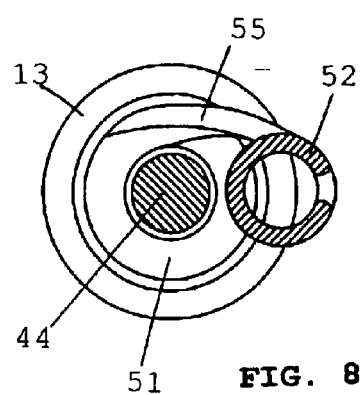
FIG. 8
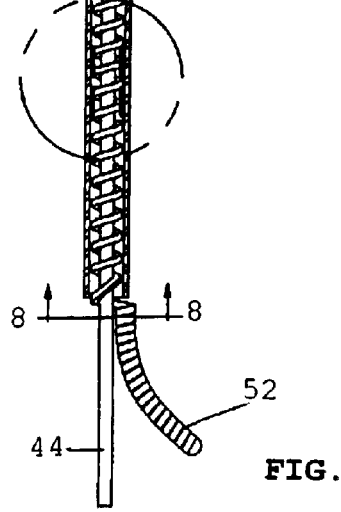
FIG. 7

US 6,818,002 B2

VESSEL CLEANER AND BARRIER

CROSS REFERENCE TO OTHER APPLICATIONS

This application is a continuation in part (CIP) of my application Ser. No. 09/867,307 filed on May 29, 2001 now U.S. Pat. No. 6,758,851 (my doc. Th5) that is a CIP of my earlier application Ser. No. 09/654,934 filed on Sep. 1, 2000 now U.S. Pat. No. 6,482,215 (my doc. Th4) that is a CIP of my earlier application Ser. No. 09/389,712 filed on Sep. 3, 1999 (my doc. Th3; now U.S. Pat. No. 6,143,009) that is a CIP 09/241,802 filed on Feb. 2, 1999 (my doc. Th2; now abandoned). This application also relies for priority on my international patent application PCT/US00/01797 filed on Jan. 25, 2000 that relies for priority on the above mentioned patent applications Ser. No. 09/389,712 and Ser. No. 09/241,802 and on a provisional application Ser. No. 60/118,611 filed on Feb. 4, 1999. Additionally this application is a CIP of my earlier application Ser. No. 10/086465 (my doc. Cth1), filed on Mar. 1, 2002 now U.S. Pat. No. 6,767,353.

All the above prior applications are being incorporated herein by reference.

BACKGROUND AND SUMMARY OF THE INVENTION

The rotary flexible-agitator system is designed for removing an obstruction from within a patient's vessel through a tube of small diameter and particularly for opening vessels, such as blood vessels, that tend to become obstructed by a thrombi.

Current treatments such as pharmacological, surgical or trans-catheter procedures can be time-consuming, traumatic and expensive. Thus, objects of the present invention are to simplify, improve and shorten the process by enabling the physician to navigate and thread the system through obstructions, curved vessels and bifurcations and then break the obstruction to small pieces that are simultaneously removed through the tube by a combination of suction and mechanical means. To further reduce the likelihood of pieces of the obstruction being carried down stream into the vasculature the system can be delivered through a guiding catheter with a distal barrier that temporarily occludes flow through the vessel during the procedure. These and other objects of the invention will become apparent from the following discussion and the accompanying drawings.

BRIEF DESCRIPTION OF THE FIGURES

In the following FIGS. the midsection of the embodiments is represented by an intermittent line to enable to fit the FIGS. on the drawing sheet and the embodiments' distal section is enlarged to show certain details.

FIG. 1 shows a cross section view of a first embodiment having a flexible tube and a offset distal agitator extending out of the open distal end of the flexible tube, inserted into a curved vessel through a catheter with a distal barrier.

FIG. 2 shows an enlarged cross section of the system as viewed on a cross-sectional plane 2—2 (note FIG. 1).

FIG. 3 shows a further enlarged sectional view of a portion of the expandable balloon.

FIG. 4 shows the first embodiment with the offset distal-agitator being pulled into the flexible tube causing its effective diameter to decrease.

FIG. 5 shows a cross-sectional view of modified first embodiment that is equipped with ferrules to limit the extension of the agitator-shaft from over-extending out of the flexible tube.

FIG. 6. shows an enlarged cross-section of a portion of the embodiment of FIG. 5 that is marked by an oblong circle and contains the ferrules.

FIG. 7 shows a second embodiment of the invention, where the system is deliverable into the vessel over a guidewire FIG. 8 shows a cross section of the agitator-shaft as viewed on a cross-sectional plane 8—8 as marked on FIG. 7.

FIG. 9. shows an enlarged cross-section of a portion of the embodiment of FIG. 7 that is marked by a circle and contains the ferrules.

DETAILED DESCRIPTION

FIGS. 1, 2 and 3 shows a rotary flexible agitator system and barrier 10 for removing an obstruction 19 (e.g., thrombus) from within a patient's vessel 11 (same items will be marked with same numbers throughout the FIGS.). It comprises a tubular housing 12 having a flexible tube 13 with an open distal end 14 and a proximal end section 15 with a suction port 16. A rotary flexible agitator-shaft 17, coupled to and driven by an electric motor 29, is disposed in the tubular housing. The agitator-shaft has an offset distal-agitator 18 attached to its distal end that extends out of the open distal end. The effective diameter of the offset distal-agitator is substantially larger than the diameter of its cross section. Rotating the offset distal-agitator breaks the obstruction in the vessel to pieces and the relative motion between the rotary flexible agitator-shaft and the flexible tube reduces the longitudinal friction that may resist the movement of the pieces through the flexible tube as further explained in my U.S. Pat. No. 6,143,009.

The flexible agitator-shaft is moveable relative to the flexible tube to thereby pull or push the offset distal agitator in or out of the flexible tube as shown in FIG. 4 and as further explained in my co-pending parent application Ser. No. 09/867,307 (note FIG. 3 in the parent case).

The flexible tube 13 is disposed in a catheter 20 having an expandable distal barrier 21 for temporarily occluding the vessel. The barrier preferably comprises a selectively inflatable balloon 22 with a toroidal (donut-like) shape that is attached to the distal end section of the catheter. A passage 23, defined in the wall of the catheter 24, connects the balloon to a port 25 to which an inflation device such as a syringe (not shown) can be connected to effect inflation or deflation of the balloon. The catheter has an additional port 26 that communicates with the vessel through a main lumen 27 of the catheter. The agitator-shaft preferably comprises a spiral wire 28. The agitator-shaft and offset distal-agitator can be made of one continuous wire (see FIG. 5). The agitator-shaft and the offset distal-agitator are made from one continuous flattened wire wound on its edge and the distal-agitator is made from the flattened wire wound on its side, as shown in FIG. 5.

The cross-section of the agitator shaft is larger than the cross-section of the offset distal-agitator as also shown in FIG. 5.

A first ferrule 31 having a first internal diameter 32 and a first bearing surface 33 is fitted inside and attached to the flexible tube. A second ferrule 34 having a second bearing surface 35 and a second external diameter 36 is fitted over and attached to the spiral wire. The second external diameter is larger than the internal diameter. The first bearing surface is located at a first distance 37 from the open distal end and the second bearing surface is located at a second distance 38 from the open distal end, whereas the second distance is not smaller than the first distance. As the bearing surfaces come in contact the extension of the agitator-shaft out of the flexible tube is limited. Absent the ferrules an agitator-shaft, especially in long version of the system, may become extended in the process of conveying debris or due to external forces.

FIGS. 7, 8 and 9 shows a second embodiment 50 that can be delivered into the vessel over a guidewire 44 or a similarly elongated flexible component. In order to provide a distal opening for the guidewire a spiral wire 51 is transitioned to an offset distal-agitator 52 that is shifted sideways as shown in FIG. 8. The shift is achieved by slightly elongating the transitional section 55 (as compared to the transitional section 38 in the parent case Ser. No. 09/867,307). The proximal end of the second embodiment 56 is similar to the proximal end of the shown in the parent case (less the illumination means 77) to which reference is made for further construction details.

Another aspect of the invention is a method of removing an obstruction from a vessel comprises the following steps: inserting into the vessel a distal end of a catheter having an expandable distal barrier, inserting into the vessel a rotary flexible-agitator system comprising a tubular housing having a flexible tube with an open distal end and a proximal end section with a suction port, a motor driven rotary flexible agitator-shaft disposed in the tubular housing, the agitator having an offset distal-agitator attached to its distal end, temporarily occluding the vessel by expanding the distal barrier, rotating the offset distal-agitator that extends out of the open distal end, and has an effective diameter substantially larger than its cross section, to break the obstruction in the vessel to pieces, the relative motion between the rotary flexible agitator and the flexible tube reducing the longitudinal friction that may resist the movement of the pieces through the flexible tube The catheter is preferably inserted into the vessel through a standard introducer 42, which can have a port 43 through which fluid is introduced into or withdrawn from the vessel.

While the present invention has been illustrated by a limited number of embodiments, it should be understood that modifications and substitutions may be made within the spirit of the invention and the scope of the claims.

What is claimed is:

1. A process of removing an obstruction from a vessel comprising the following steps:
    inserting into the vessel a distal end of a catheter having an expandable distal barrier;
    inserting into the vessel a rotary flexible agitator system comprising a tubular housing having a flexible tube with an open distal end and a proximal end section with a suction port, a motor-driven rotary flexible agitator-shaft disposed in the tubular housing, the agitator-shaft having an offset distal-agitator attached to its distal end;
    temporarily occluding the vessel by expanding the distal barrier;
    rotating the offset distal-agitator that extends out of the open distal end, and has an effective diameter substantially larger than its cross section, to break the obstruction in the vessel to pieces, the relative motion between the rotary flexible-agitator and the flexible tube reducing the longitudinal friction that may resist the movement of the pieces through the flexible tube.

2. As in claim 1 wherein the catheter is inserted into the vessel through an introducer.

3. As in claim 2 wherein the introducer has a side arm through which fluid is introduced into or withdrawn from the vessel.

* * * * *